United States Patent
Ranoux

Patent Number: 5,084,004
Date of Patent: Jan. 28, 1992

[54] PROCESS FOR INTRA-UTERINE FERTILIZATION IN MAMMALS AND DEVICE FOR IMPLEMENTATION THEREOF

[76] Inventor: Claude Ranoux, 2 Beverly Rd., Arlington, Mass. 02174

[21] Appl. No.: 449,942
[22] PCT Filed: May 2, 1988
[86] PCT No.: PCT/FR88/00212
§ 371 Date: Dec. 29, 1989
§ 102(e) Date: Dec. 29, 1989
[87] PCT Pub. No.: WO88/08280
PCT Pub. Date: Nov. 3, 1988

[30] Foreign Application Priority Data
Apr. 30, 1987 [FR] France ............... 87 06205

[51] Int. Cl.⁵ .......................... A61B 17/43
[52] U.S. Cl. ............................. 600/34; 128/898; 128/899; 604/890.1; 604/54; 604/906
[58] Field of Search ............... 600/33-35; 128/898, 899; 604/890.1-892.1, 48-55, 279, 19, 906, 403

[56] References Cited

U.S. PATENT DOCUMENTS

| | | |
|---|---|---|
| 3,910,275 | 10/1975 | Babey et al. |
| 4,093,708 | 6/1978 | Zaffaroni et al. ......... 604/892.1 |
| 4,380,997 | 4/1983 | Leibo . |
| 4,419,986 | 12/1983 | Leibo ................... 600/34 |
| 4,677,967 | 7/1987 | Zarfman ................ 600/35 |
| 4,701,161 | 10/1987 | Lenck .................. 600/34 |
| 4,790,814 | 12/1988 | Fischl et al. ........... 600/35 |
| 4,865,589 | 9/1989 | Simmet et al. .......... 604/906 |
| 4,902,286 | 2/1990 | Ranoux ................ 600/33 |
| 4,940,465 | 7/1990 | Theeuwes et al. ....... 604/892.1 |

FOREIGN PATENT DOCUMENTS

| | | |
|---|---|---|
| 0066488 | 12/1982 | European Pat. Off. . |
| 1616899 | 11/1970 | Fed. Rep. of Germany . |
| 2539628 | 7/1984 | France . |
| 2574656 | 6/1986 | France ................. 600/35 |
| 2589879 | 5/1987 | France . |
| WO83/02386 | 7/1983 | PCT Int'l Appl. . |
| 1287873 | 2/1987 | U.S.S.R. ............... 600/35 |

OTHER PUBLICATIONS

"Human Pregnancy Following Oocyte and Sperm Transfer to the Uterus", *The Lancet Ltd.*, May 8, 1982, by I. Craft et al., pp. 1031–1033.

Primary Examiner—Randall L. Green
Assistant Examiner—K. Reichle
Attorney, Agent, or Firm—Young & Thompson

[57] ABSTRACT

The fertilization process comprises the following steps: a) a container (15) which can be introduced into, and lodged in, the uterine cavity of the mammal is provided; b) the container (15) is filled with a culture medium, at least one ovocyte of the mammal, and spermatozoa; c) the filled container (15) is inserted in the uterine cavity; d) the container (15) is left for a given length of time to allow fertilization of the ovocyte(s) to take place; e) the contents of the container (15) are released into the uterine cavity. The container may be made from a tube of biodegradable or non-biodegradable material. In the latter case, it is associated with a stiffening device. A biodegradable container (15) filled with gametes and a culture medium is placed in the uterine cavity using an implantation device (20) which is then withdrawn from the mammal's genital tract.

36 Claims, 2 Drawing Sheets

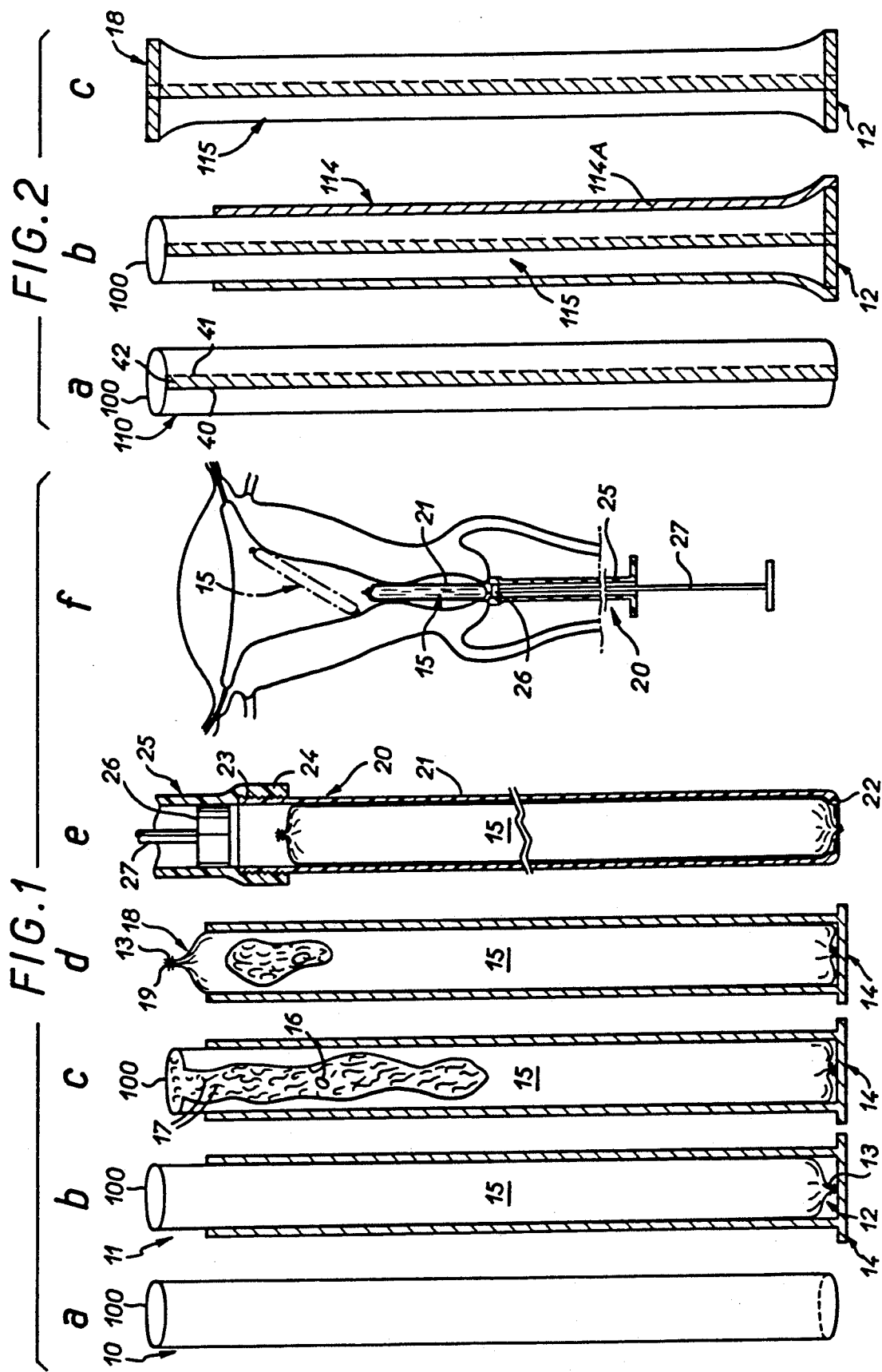

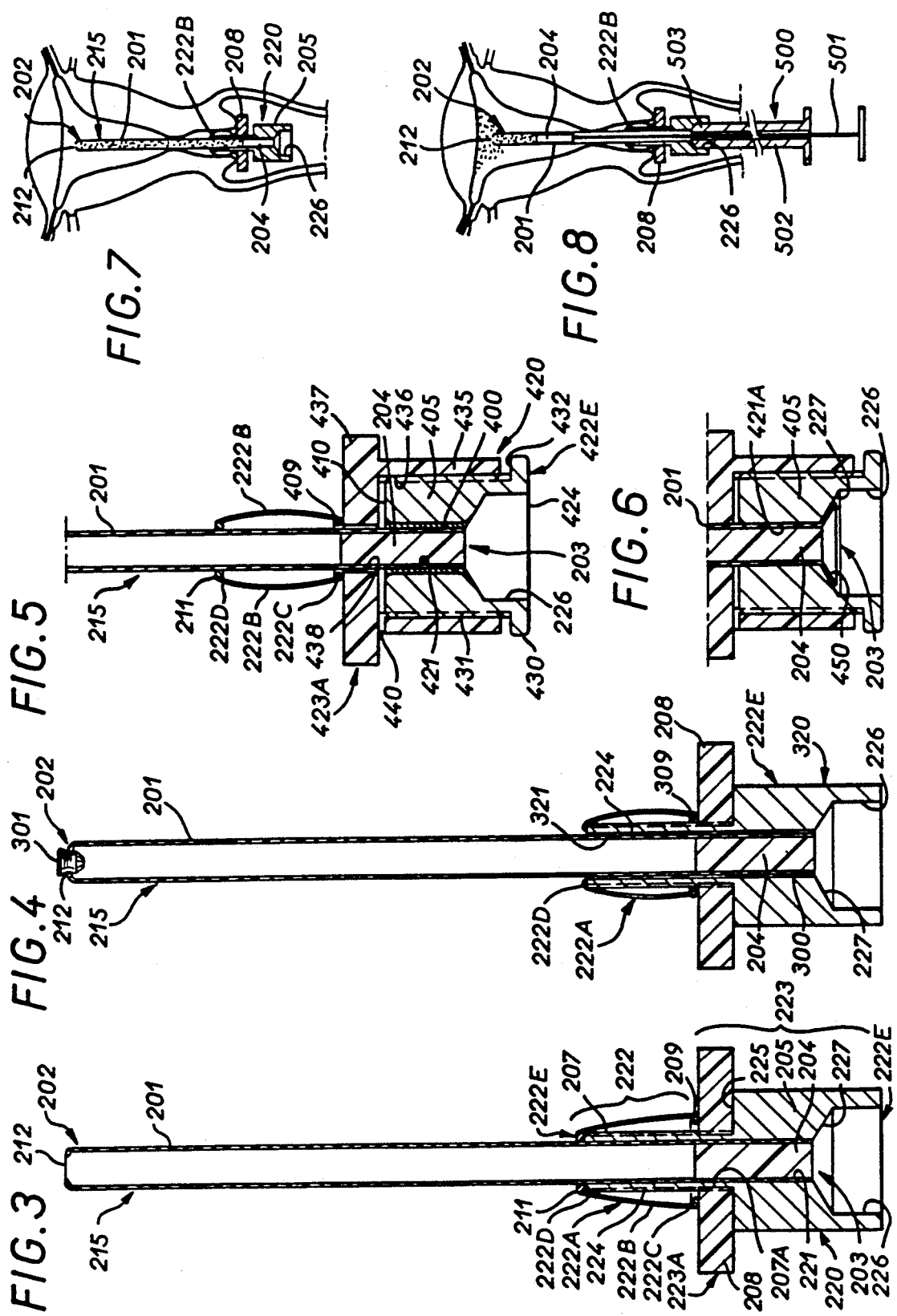

PROCESS FOR INTRA-UTERINE FERTILIZATION IN MAMMALS AND DEVICE FOR IMPLEMENTATION THEREOF

FIELD OF THE INVENTION

The present invention concerns a fertilisation process for mammals and a device for implementation thereof.

THE KNOWN PRIOR ART

The applicant has previously described a human fertilisation process using a container in patent applications FR-85 16558 and PCT/FR 86 00378.

In this process, ovocytes are removed from a patient in the normal manner, in general using echographic monitoring. The patient initially undergoes ovarian stimulation using Clomid-HMG or LH-RH agonists such as busereline and DTR-P-6.

Follicular liquid is taken into a syringe and immediately examined in the laboratory.

Up to eight ovocytes are then placed in a container constituted by a tube which is open at one end and completely filled with culture medium, for example MENEZZO culture medium B2, containing 10,000 to 20,000 mobile human spermatozoa per milliliter. The tube is then hermetically sealed without the interposition of air, i.e. with no layer of air above the liquid phase.

The sealed tube is then placed in the patient's vaginal cavity for 44 to 50 hours. The tube is then retrieved, opened and the ovocytes are examined in the laboratory.

Fertilised ovocytes which have already started to divide are embryos in their first stages of development.

Up to four of these embryos are then replaced in the patient's uterine cavity using a Frydman catheter.

This CIVETE (intravaginal culture and embryonic transplantation) technique has shown cleavage rates, transfer rates and surgical birth rates at least equal to those obtained using the FIVETE (in vitro fertilisation and embryonic transplantation) technique.

In the CIVETE technique, up to eight ovocytes are placed in a container containing 3.2 ml liquid constituted by medium B2 containing 10,000 to 20,000 mobile spermatozoa per milliliter. The mean volume of liquid per ovocyte is thus 400 microliters, containing 4,000 to 8,000 mobile spermatozoa.

Whilst the CIVETE technique has a number of advantages over the FIVETE technique as it does not require an incubator with an atmosphere of $CO_2$-enriched air, there are a few disadvantages. The number of stages of manipulation of male and female gametes is still high and in particular the technique necessitates replacement of one or more embryos in the uterus. Such a number of stages leads to toxicity or even to embryo loss.

SUMMARY OF THE INVENTION

In order to overcome the disadvantages briefly mentioned above the Applicant proposes a process of fertilisation in mammals which is characterised in that it comprises the following steps:

a) providing a container which can be introduced into and lodged in the uterine cavity of the mammal;

b) filling the container with a culture medium, at least one ovocyte of the mammal and spermatozoa;

c) inserting the filled container into the uterine cavity;

d) leaving the container for a specific period of time to allow fertilisation of the ovocyte(s) therein;

e) allowing the contents of the container to escape into the uterine cavity.

This method avoids in particular the final step of embryo transfer from outside the mammal to the interior of the uterine cavity.

According to a preferred feature of the process of the invention, said escape is effected by ejecting the container contents into the back of the uterine cavity in order to increase the chances of implantation of fertilised ovocytes or embryos.

For the same reasons, if the container is of biodegradable-material it is still preferable to insert it towards the back of the uterus.

This process requires a container of a size which is suitable for introduction into and lodging in the uterine cavity of a mammal. It must be much smaller than a container for the FIVETE technique, particularly for human females, as the neck of the human uterus has an opening of only a few millimeters.

The method described above has been developed by the Applicant in work conducted since December 1986 in the form of preliminary studies involving a process comprising the following steps:

1. providing a fine tube having a capacity of about 250 microliters;

2. filling the tube with a culture medium, at least one human ovocyte and mobile human spermatozoa;

3. closing at least one end of the tube and immersing the other end in a receptacle containing culture medium;

4. placing the filled tube and its receptacle in an oven at 37° C. for 20 to 30 hours;

5. collecting the embryos and placing them in culture medium in the incubator at 37° C. until the following day;

6. replacing one or more embryos in the uterine cavity of the patient using a Frydman catheter.

The embryo(s) are replaced 44 to 50 hours following filling the tube with the mixture of culture medium, ovocyte(s) and spermatozoa.

These preliminary studies showed that in tests covering 57 ovocytes 33 were fertilised to give embryos for replacement (a cleavage rate of about 58%), whilst of 88 ovocytes removed in similar manner followed by in vitro fertilisation (IVF) or intravaginal culture (IVC), 44 embryos for replacement were produced, i.e. a cleavage rate of 50%. Two pregnancies can certainly be attributed to replacement of fine tube fertilised ovocytes.

These preliminary studies showed that up to four human ovocytes can be fertilised in a fine tube of this kind. It has been shown that fine tube fertilisation of this kind requires an average volume of culture medium per ovocyte of only about 60 microliters, containing 600 to 1,200 mobile spermatozoa. The culture medium used in these studies was MENEZZO culture medium B2.

The present invention also proposes a container for carrying out the intra-uterine fertilisation process according to the invention, characterised in that it is of a size which enables it to be inserted into and lodged in the uterine cavity of a mammal and which also enables it to receive a culture medium, at least one ovocyte and spermatozoa and in that it comprises means for defining an exit area for at least one fertilised ovocyte into the uterine cavity distanced from the neck of the uterus.

According to one aspect of the invention the container is made entirely of biodegradable material. This has the advantage that the container filled with culture medium and gametes can be introduced into the uterine cavity with no further intervention for implantation of the embryo(s).

According to another aspect of the invention a non-biodegradable container is associated with a holding device which can be removably fixed to the neck of the uterus of the mammal.

This avoids the possibility of losing the non-biodegradable container in the uterine cavity and also enables positioning of the exit area of the container towards the back of the uterus to improve the chances of implantation.

According to a further aspect of the invention, the container is a tube closed at one, so-called lower end by a plug acting as a watertight piston, the tube being fastened to the holding device towards its lower end by means of a longitudinal bore through the latter.

These features allow an operator to eject the container contents at the appropriate moment by manipulating the plug acting as a piston, as will be described below.

Since the holding device extends out of the uterus, the plug is readily accessible through the vagina.

BRIEF DESCRIPTION OF THE DRAWINGS

The present invention will be better understood by the following description with reference to the appended drawings wherein:

FIGS. 1a, b, c, d, e, f show enlarged cross-sectional views of a first embodiment of a container according to the invention formed from a tube of biodegradable material and insertion of the filled container in the uterine cavity of a patient;

FIGS. 2a, b, c show a second embodiment of a container according to the invention formed from a thin sheet of biodegradable material;

FIG. 3 shows a schematic longitudinal cross-section through a third embodiment of a container associated with a holding device for retaining it in the neck of the uterus of the mammal;

FIG. 4 shows a longitudinal cross-section of a variant of the container embodiment associated with the holding device from FIG. 3, with a biodegradable plug;

FIG. 5 shows a longitudinal cross-section of a further embodiment of a container associated with a holding device for retaining it in the neck of the uterus of the mammal;

FIG. 6 shows a variant embodiment of the container and its associated holding device from FIG. 5;

FIG. 7 shows schematically the container and the holding device from FIG. 3, the container being lodged in the uterus and held in place by the holding device fixed in the neck of the uterus;

FIG. 8 shows schematically the step of the process according to the invention wherein the container from FIG. 3 is emptied into the uterine cavity.

DETAILED DESCRIPTION OF THE DRAWINGS

FIG. 1a shows, enlarged, a cylindrical tube 10 with a length less than the depth of the uterus. The tube is produced by extrusion and has a wall 100 of constant thickness.

It is made from animal or vegetable polymer, particularly a hydrophilic polymer, for example collagen, fibrinogen or a polymeric sugar.

FIG. 1b shows a tube 11 produced from the open tube 10 by closing its lower end 12 with a knot of suture 13. Suture 13 is preferably biodegradable or even resorbable by the mammal's body. Such sutures are used in surgery as resorbable stitches. The knot turns the tube 11 into a container 15, its lower end 12 resembling the end of a sausage. The upper and lower ends of tube 10 may also be closed by welding or by gluing with a biodegradable adhesive or simply by pressure. The exit area is defined here by a wall 100 of material which will be biodegradable over a known period by the contents (culture medium, spermatozoa, ovocytes(s)) and the intra-uterine environment. Container 15 is entirely formed of material which will biodegrade over a known period.

Tube 11 is slid into a footed test tube 14 which has an internal diameter substantially equal to the external diameter of tube 11 and which acts as a support.

The footed test tube may be made of a low friction material, for example polytetrafluroethylene or polyethylene, and is slightly shorter than closed tube 11.

FIG. 1c shows, partially cut away, container 15 completely filled with culture medium, in this case MENEZZO culture medium B2, and containing an ovocyte 16 and spermatozoa 17. Test tube 14 counterbalances the hydrostatic pressure of the liquid filling container 15 and thus avoids premature rupture of the very thin container wall. The filled container closed at only one end 12 may be left as it is, the other end remaining open for insertion in the uterine cavity, provided that the contents cannot spontaneously empty out when the tube is upended and its open end directed downwards.

The container may be filled in the normal manner using a syringe where the internal diameter of the needle is greater than that of the ovocyte.

Tube 10 may also be filled by aspiration to produce the filled tube of FIG. 1c as follows:

Tube 10, open at both ends, is inserted in an elongate hollow support cylinder having an internal diameter equal to that of test tube 14 from FIG. 1b but open at both ends so that tube 10 projects from both ends of the hollow cylinder. A suction connector is then fixed to the top of the cylinder so that it is airtight and does not bend the upper end of tube 10. The lower end of tube 10 and that of the support cylinder are then immersed in culture medium B2 containing spermatozoa and one or more ovocytes. These gametes and the culture medium are sucked up to fill the tube 10 open at both ends. The lower ends are removed from the liquid and the lower end of tube 10 is closed by tying, welding or gluing before removing the suction connector from the top of the support cylinder. A filled tube is thus obtained analogous to that shown in FIG. 1c except that test tube 14 is replaced by a hollow cylinder open at both ends.

FIG. 1d shows a partially cut away view of container 15 from the preceding FIG. closed at its upper end 18 by a knot using the same resorbable suture 13. Container 15, closed at both ends 12, 18, can therefore contain a liquid without the interposition of air, if required.

When knot 18 is tied some excess fluid remains in the frustoconical section 19 of tube 10 above the upper knot.

The thickness of wall 100 of biodegradable material tube 10 of course determines the time lapse before the contents of the container can escape into the uterine cavity. In the process according to the invention, this wall must disintegrate a certain time after introduction of the sausage-like container 15 from FIG. 1d into the uterine cavity of the mammal in order that the contents may spontaneously escape into the uterine cavity after a predetermined period to enable one or more embryos to implant. This escape can be facilitated if one end of tube 11 remains open, i.e. if only one end of tube 10 is closed.

The container material must be resorbable and non-immunogenic. In this instance the container has a wall of a single thickness but it is also possible to employ a biodegradable container having walls of different thickness.

The mammalian uterus provides a warm, humid environment in the uterine cavity, but without any high enzymatic activity which will provoke degradation of a biodegradable material.

On the other hand, mobile mammalian spermatozoa are highly active enzymatically and may attack the inside of wall 100 of container 15 sufficiently to degrade and burst it.

In order to determine the wall thickness required for escape of the contents after a specified period of between 15 and 55 hours, for example, the following in vitro test is conducted:

A container having wall thickness E is produced and filled as shown in FIG. 1d with a culture medium containing 10,000 to 20,000 spermatozoa per milliliter, but no ovocytes.

This container when filled in this way is placed in an incubator saturated with water vapour at about the internal temperature of the mammal. The state of the container is observed regularly and the time at which the contents spontaneously escape from the container is noted. If this time is greater than 55 hours a further container is produced having walls thinner than E, for example 0.5E, and the above in vitro test carried out on this container. Using an iterative method a thickness of wall 100 can be obtained which produces the desired in vitro degradation time, for example 15 to 55 hours.

Wall 100 of biodegradable material tube 10, 11 may have a thickness of between 0.01 and 1 mm.

Tests have shown that MENEZZO culture medium B2 containing 10,000 to 20,000 spermatozoa per milliliter degrades in this in vitro test a cured collagen wall 0.1 mm thick in over 72 hours and a gelose wall 0.1 mm thick, as used in gastroresistant capsules, in 15 minutes.

FIG. 1e shows container 15 filled as in FIG. 1d separated from its supporting test tube 14 before introduction into an implantation device 20 comprising a cylindrical tube 21 having an internal diameter substantially equal to that of test tube 14. Cylindrical tube 21 is longer than the container 15 and its length may for example be close to or greater than the depth of the mammalian uterine cavity.

At its lower end cylindrical tube 21 comprises a rounded edge 22 which slightly reduces the diameter of the orifice in order to retain tube 15 and prevent it from sliding out. Towards its upper end tube 21 has an external screwthread 23 onto which end 24 of a cylindrical tube 25 is screwed, tube 25 having inside it a piston 26 which slides with low friction and is fixed to shaft 27. The internal diameter of cylinder 25 is equal to that of tube 21 to allow continuity of sliding movement of piston 26 in cylindrical tube 21.

FIG. 1f shows a schematic view of the introduction into and lodging of container 15 in the uterine cavity of a mammal by entry of tube 21 into the uterine cavity through the neck of the uterus.

Tube 21 is introduced into the uterine cavity so as to leave sufficient depth for filled container 15 to lodge therein, and piston 26 then is pushed using shaft 27 which protrudes from the body of the mammal, as does cylindrical tube 25. This deposits container 15 near the back of the uterus. The implantation device 20 is then withdrawn from the uterus and vagina of the mammal and the contents of filled container 15 escape after a period determined by biodegradation of at least one part of the container.

FIGS. 2a, b, c show another embodiment of a biodegradable material container.

FIG. 2a shows how a hollow elongate tube 110 is formed from a thin strip of biodegradable material. This strip may, for example, be rolled around a solid cylindrical mandrel (not shown) and edges 40 and 41 may overlap slightly to produce a common contact area 42 which can be bonded using a biodegradable adhesive or pressure or heat welded.

The tube 110 has a thin wall 100, common area 42 being thicker.

Like tube 10, tube 110 may be filled by aspiration of a culture medium containing spermatozoa and at least one ovocyte.

FIG. 2b shows the lower end of tube 110 closed by clamping or bonding to form a container 115 which can be held in a support 114 which is flared and open at the base.

Support 114 is slightly shorter than container 115.

In addition, support 114 can be separated into two shells 114A to release container 115.

FIG. 2c shows container 115 filled, closed by clamping or bonding its upper end 18 and ready for insertion into the uterine cavity of the mammal using an implanting device similar to implanting device 20.

FIG. 3 shows a container 215 associated with a support decice 220 which can be removably fixed in the neck of the mammal's uterus. This container is a tube 201 formed from a synthetic material which cannot be biodegraded by spermatozoa, for example polyethylene or polypropylene which has no toxic effects on the spermatozoa, the ovocytes or the mammal itself.

The tube is flexible and unbreakable to enable it to deform during its difficult passage through the neck of the uterus and to adapt to the internal shape of the uterine cavity of the mammal. Tube 201 has a so-called upper open end 202 which may be closed by a small plug (not shown) of biodegradable material, for example collagen, fibrinogen or a polymeric sugar.

Open end 202 has a restricted orifice 212 as compared with the internal diameter of tube 201.

The other, so-called lower end 203 of the tube is closed by a plug 204 which forms a watertight piston inside tube 201.

Tube 201 has a length about equal to the depth of the uterine cavity of the mammal.

For a patient tube 201 may be between 5 and 7 cm long and have an exterior diameter of up to 3 mm to enable it to be slid into the uterine cavity through the neck of the uterus without causing any trauma.

Tube 201 is fixed to holding device 220 over a portion of its length near its lower end 203 by means of a longitudinal bore 221 passing through the holding device.

Holding device 220 comprises, in longitudinal succession, a first section 222 which can be introduced into the neck of the uterus and a second section 223 which can be located in the vagina external to and abutting the cervix. The first section comprises a radially expansible element 222A having a rest position for insertion into the cervix and a second position in which it presses against the internal walls of the neck of the uterus.

Expansible element 222A is formed of thin walled flexible material which can expand radially into the second position.

The expansible element comprises at least two longitudinal tangs 222B each having a movable lower end 222C and an upper end 222D which is fixed longitudinally relative to tube 201.

Holding device 220 further comprises a mobile portion 223A for controlling the longitudinal position of the lower end 222C of expansible element 222A and a portion 222E which is fixed relative to tube 201 and on which mobile portion 223A can move.

In more detail, fixed portion 222E comprises a longitudinal cylindrical extension 224 forming part of said first section 222 of holding device 220. Screwthread 207 is carried on the external surface of extension 224.

Cylindrical extension 224 is formed in one piece with a cylindrical sleeve 205 of greater diameter. Where they join, a shoulder 225 is formed on the upper external surface of sleeve 205.

Extension 224 and sleeve 205 are formed with a first bore 221 having a slightly smaller diameter than the external diameter of tube 201 so that the latter can be forced into the bore and retained therein.

Sleeve 205 comprises a second bore 226 having a larger diameter than the outside diameter of tube 201, the first bore opening into the second through a frustoconical cavity 227.

Second bore 226 has a depth and diameter sufficient to receive a pusher device for displacing plug 204 in tube 201.

Mobile portion 223A comprises a knurled disc 208 which can screw onto screwthread 207 because it has a complementary screwthread 207A.

Thus fixed section 222B and mobile section 223A comprise complementary screwthreads 207, 207A to allow the mobile section to turn and to move longitudinally relative to the fixed section.

FIG. 3 shows that knurled disc 208 has a diameter sufficient to abut the neck of the uterus. In its lowest position on the complementary screwthread 207, one of the faces of the knurled disc is in contact with shoulder 225. A so-called lower ring 209 around cylindrical extension 224 rests on the other, broadly circular side of the disc.

Tube 201 comprises a welded collar 211 which substantially abuts the top of cylindrical extension 224.

Each tang 222B is fixed at its lower end 222C to lower ring 209 and at its upper end to welded collar 211. The upper end of expansible element 222A is therefore fixed to collar 211 welded to tube 201. Each tang is very slightly curved with its concave side oriented towards cylindrical extension 224.

Thus if ring 209 and collar 211 are brought closer together the curvature of the tangs 222B, their radial extension and flexion increase.

FIG. 4 shows a variant embodiment of tube 201 associated with holding device 320.

The upper end 222D of expansible element 222A is attached to the upper end of cylindrical extension 224 of fixed portion 222E. This eliminates the need for the welded collar of the preceding embodiment.

Longitudinal bore 321 through holding device 320 has a diameter which is slightly greater than the external diameter of tube 201 so that the latter can be joined to fixed part 222E by adhesive 300.

Lower ring 309 which rests on knurled disc 208 has a slightly smaller diameter to that of ring 209 from the preceding figure, but it is still slidable longitudinally on cylindrical extension 224.

Orifice 212 at the upper end 202 of tube 201 is closed by a plug 301 of biodegradable material the same as that described above. The shape of the plug is such that it can be readily expelled when the liquid contents of the container are ejected on upward displacement of piston 204 inside the tube towards the upper end 202 of tube 201.

FIG. 5 shows another embodiment of tube 201 and holding device 420.

Tube 201 comprises a welded collar 211 attached to the upper end 222D of each tang 222B, the lower ends 222C of which are fixed to a ring 409 which is slidable on tube 201.

In this preferred embodiment, the cylindrical extension of the preceding embodiments is dispensed with.

Holding device 420 comprises a cylindrical sleeve 405 comprising, starting from its upper circular surface 410, an axial bore 421 having a depth of about half the longitudinal height of sleeve 405.

The diameter of bore 421 of length l is about the same as the external diameter of tube 201 and enables sleeve 405 to be fixed to the corresponding lower end of tube 201 over a length l by glue 400.

Bore 421 opens into a longitudinal bore 226 through a frustoconical portion 227. Bore 226 opens into the lower circular surface 424 of sleeve 405. As in the embodiments of FIGS. 3 and 4, bore 226 and frustoconical portion 227 which prolongs it can removably receive a suction nozzle if plug 204 which closes the lower end 203 of tube 201 is tripartite (plug as used in CASSOU tubes in France). Alternatively, bore 226 and frustoconical portion 227 can receive the end of a sliding shaft pusher device which can displace piston plug 204 inside and towards the upper end 202 of tube 201.

Aligned with and extending from the lower surface 424 of sleeve 405 is a flange 430 to facilitate handling.

A screwthread 431 is provided over the full height of the outer cylindrical surface of sleeve 405. It stops near the base of shoulder 432 formed by flange 430.

Screwed on sleeve 405 is a bush 435 whose internal cylindrical surface carries a screwthread 436 complementary to screwthread 431 on sleeve 405.

The longitudinal depth of bush 435 is substantially equal to the height of the sleeve less the height of flange 430.

The top of bush 435 is in one piece with and closed by a knurled disc 437. The disc diameter is greater than that of the bush to facilitate manipulation of the knurled disc. Disc 437 comprises a cylindrical axial passage 438 whose diameter is slightly greater than the external diameter of tube 201 to permit sliding contact. To facilitate equilibrium of the pressure in the cavity defined between circular surface 410 of sleeve 405 and the base of bush 435 defined by disc 437, a hole 440 is provided in the cylindrical wall of bush 437 in the immediate vicinity of the base.

Thus in this embodiment, fixed section 422E and mobile section 423A comprise complementary screwthreads 431, 436 so that the mobile section can turn and move longitudinally relative to the fixed section.

Screwthreads 431, 436 are respectively on an external cylindrical surface of fixed section 422E and on an internal cylindrical surface of a bush 435 on mobile section 423A.

FIG. 6 shows a variant of the preceding embodiment wherein the lower end 203 of tube 201 comprises a flange 450 which matches the shape of a part of the conical surface of the frustoconical cavity portion joining bore 421A to bore 226 for the connector.

This flange 450 is intended to increase the integrity of tube 201 with sleeve 405 by preventing longitudinal displacement of the tube from bore 226 into bore 421A. In this case the tube is simply crimped into bore 421A.

FIGS. 7 and 8 show container 215 and holding device 220 from FIG. 3 holding the container in position in the neck of the uterus.

The fertilisation process using the device of FIG. 3 is described below. The skilled person will readily be able to adapt the process for the other devices described with reference to FIGS. 4, 5 and 6.

If plug 204 is a tripartite plug of a type used in French CASSOU tubes, a syringe connector is inserted in bore 226 of sleeve 205 and culture medium, ovocyte(s) and spermatozoa are sucked into container 215 consisting of tube 201, via its upper end 202.

If the plug is not a tripartite plug the same contents can be introduced into tube 201 using a syringe and needle.

If required, the tube is then plugged at its upper end 202 using a plug of biodegradable material (not shown in FIGS. 7 and 8).

The device constituted by container 215 and its holding device 220 is introduced into the vagina of the mammal.

End 202 of tube 201 is introduced into the neck of the uterus and the device is pushed in until knurled disc 208 abuts the neck of the uterus.

Sleeve 205 is then held against rotation using forceps (not shown) and knurled disc 208 is moved away from shoulder 225 by turning it on screwthread 207, thus increasing the flexion of the two tangs 222B which then press against the internal walls of the neck of the uterus, thus removably fixing the holding device 220 of container 215 in the neck of the uterus. FIG. 7 shows that the length of tube 201 is preferably selected so that its upper end 202 is situated near the back of the uterus. After removing the forceps the mammal is allowed to rest for 15 to 55 hours to obtain one or more embryos in tube 201.

FIG. 7 shows this rest stage.

FIG. 8 shows the contents of container 215 being ejected after this period into the back of the uterine cavity, after fertilisation of one or more ovocytes, by pushing plug 204 towards the upper end 202 of tube 201 to place the contents of container 215 directly in contact with the endometrium to implant one or more embryos. The plug is pushed using a pusher device 500 comprising a flexible shaft 501 which can move in a sheath 502. Connector 503 of sheath 502 fits closely into bore 226.

Shaft 501 has a smaller diameter than the internal diameter of tube 201 and its length is such, in relation to the lengths of casing 502, plug 204 and tube 201, that plug 204 cannot pass out of tube 201 through its end 202. The restricted orifice 212 also acts as a security measure to keep the plug in the tube.

Knurled disc 208 is then unscrewed to release tangs 222B and free holding device 220. The apparatus is then removed from the genital tract of the mammal.

The holding devices have been described with reference to FIGS. 3 and 6 as comprising two tangs 222A. It is possible to use three or more tangs regularly distributed about tube 201.

I claim:

1. Process of intra-uterine fertilization in mammals comprising the following steps
   a) providing a container of a size suitable for introduction and lodging in the uterine cavity of a mammal and having an exit area;
   b) filling the container with culture medium, at least one ovocyte of the mammal and spermatozoa;
   c) introducing and lodging the filled container in the uterine cavity;
   d) leaving the container lodged in the uterine cavity for a specified period of time to allow fertilization of the at least one ovocyte therein; and
   e) accessing the uterine cavity through the exit area of the container without removal of the container from the uterine cavity to enable transfer of the at least one fertilized ovocyte through the exit area into the uterine cavity without removal of the at least one fertilized ovocyte from the uterine cavity between fertilization and transfer.

2. Process according to claim 1, wherein the uterine cavity is accessed upon completion of the introduction and lodging steps.

3. Process according to claim 1, further comprising temporarily closing off the exit area with a plug before the container is lodged in the uterine cavity, wherein the accessing step comprises expelling the plug from the exit area.

4. Process according to claim 1, further comprising, upon accessing the uterine cavity through the container, ejecting the contents of the container into the back of the uterine cavity.

5. Process according to claim 1, the exit area being defined by a biodegradable portion of the container, wherein the accessing step comprises biodegradation of the biodegradable portion.

6. Process according to claim 5, wherein the container is lodged towards the back of the uterine cavity.

7. Process according to claim 1, further comprising holding the container lodged at the neck of the uterine cavity during steps c) and e).

8. Process according to claim 1, wherein the container is lodged in the uterine cavity so that the exit area is disposed relatively adjacent the back of the uterine cavity.

9. Device for intra-uterine fertilization in mammals comprising container means sized for introduction and lodging in the uterine cavity of a mammal and for containing a culture medium and at least one ovocyte of the mammal and spermatozoa while introduced into and lodged in the uterine cavity of the mammal for a time period sufficient to allow fertilization of the at least one ovocyte, said container means including means for defining an exit area to allow access to the uterine cavity from the container means without removal thereof from the uterine cavity and enabling transfer of the at least one fertilized ovocyte from the container means into the uterine cavity without removal thereof from the uterine cavity between fertilization and transfer.

10. Device according to claim 9, wherein said means for defining an exit area comprising a permanent opening in said container means.

11. Device according to claim 9, wherein said means for defining an exit area comprises biodegradable means defining a portion of the container means which is biodegradable through contact with its contents and/or the intra-uterine environment for providing access to the uterine cavity after fertilization of the at least one ovocyte.

12. Device according to claim 11, wherein said biodegradable means comprises temporary sealing means at the exit area.

13. Device according to claim 11, wherein said biodegradable means is a wall portion of the container means.

14. Device according to claim 13, wherein the biodegradable means has a biodegradable period of 15 to 55 hours.

15. Device according to claim 13, wherein the biodegradable thickness of the biodegradable means is between 0.01 and 1 mm.

16. Device according to claim 11, wherein the container means is substantially entirely formed of biodegradable material and the biodegradable means is a part thereof.

17. Device according to claim 11, wherein the biodegradable material is a natural animal or vegetable polymer.

18. Device according to claim 17, wherein the natural polymer is selected from a group consisting of collagen, fibrinogen and a polymeric sugar.

19. Device according to claim 9, wherein said means defining an exit area is temporarily closed by a biodegradable plug adapted to be expelled from the container means.

20. Device according to claim 9, further comprising means for ejecting the contents of the container means including the at least one fertilized ovocyte into the uterine cavity.

21. Device according to claim 20, further comprising means for holding the device in the neck of the uterine cavity when the container means is lodged in the uterine cavity and the contents are ejected into the uterine cavity.

22. Device according to claim 9, further comprising means for introducing the container means into the neck of the uterine cavities and transferring it to the uterine cavity.

23. Device for intra-uterine fertilization in mammals comprising a tube means sized for introduction through the neck of the uterine cavity of the mammal into the uterine cavity and for accommodating culture medium, at least one ovocyte and spermatozoa of the mammal while lodged in the uterine cavity for a time sufficient to allow for fertilization of the at least one ovocyte therein, piston means disposed proximate one end of the tube means, said piston means being mounted for sliding movement towards the other end of the tube means, holding means for removably holding the device in the neck of the uterine cavity and for lodging the tube means in the uterine cavity, and means proximate the other end of the tube means adapted to face the back of the uterine cavity for defining an exit area to allow access to the uterine cavity without removing the tube means from the uterine cavity and enabling transfer of the at least one fertilized ovocyte from the tube means into the uterine cavity without removal thereof from the uterine cavity between fertilization and transfer, said piston means being movable toward the other end to expel the at least one fertilized ovocyte from said tube means.

24. Device according to claim 23, wherein a flange is disposed proximate to the one end of said tube means.

25. Device according to claim 23, wherein a plug of biodegradable material is disposed at the exit area for temporarily closing off the tube means, said plug being adapted to be injected in response to the movement of the piston means towards said other end of said tube means and incipient expulsion of the contents thereof.

26. Device according to claim 23, wherein said tube means is received in a longitudinal bore formed in said holding means and fastened thereto.

27. Device according to claim 23, wherein said holding means comprises a first section adapted to be received in the neck of the uterine cavity and a second section adapted to abut against the cervix, the first section comprising a flexible expansible element having a rest position for insertion and an operating position for bearing against the internal walls of the neck of the uterine cavity.

28. Device according to claim 27, wherein the flexible expansible element expands radially from the rest position to the operating position.

29. Device according to claim 27, wherein the expansible element comprises at least two substantially longitudinal tangs, first ones of the ends of said longitudinal tangs being disposed relatively adjacent said holding means and being movable relative to said tube means, and second ones of the ends being fixed longitudinally relative to said tube means.

30. Device according to claim 29, wherein the second ends of the tangs are fixed to a collar secured to said tube means.

31. Device according to claim 29, wherein said holding means further comprises a mobile section to control the longitudinal position of the first ends of the expansible element and a section fixed relative to said tube means on which the mobile section is movable.

32. Device according to claim 31, wherein the fixed section and the mobile section comprise complementary screwthreads which allow the mobile section to turn and move longitudinally relative to the fixed section.

33. Device according to claim 32, wherein the screwthreads are on an external surface of the fixed section and on an internal surface of a bush on the mobile section.

34. Device according to claim 32, wherein said mobile section comprises a knurled disc on a longitudinal extension of the fixed section, the extension comprising on an external surface having a complementary screwthread cooperable with that of the knurled disc.

35. Device according to claim 34, wherein the second ends of the tangs of the flexible expansible element are attached to a corresponding end of the extension of the fixed section.

36. Device according to claim 31, wherein the fixed section comprises a bore of greater diameter than the tube means for receiving a pusher device for displacing the piston means towards the other end of said tube means.

* * * * *